United States Patent [19]

Cohnen

[11] 4,358,460

[45] Nov. 9, 1982

[54] SUBSTITUTED 3-ARYL-2-CYCLOALKEN-1-ONE AND METHOD OF PREPARATION THEREOF

[75] Inventor: Erich Cohnen, Hamburg, Fed. Rep. of Germany

[73] Assignee: Beiersdorf Aktiengesellschaft, Fed. Rep. of Germany

[21] Appl. No.: 248,928

[22] Filed: Mar. 30, 1981

[30] Foreign Application Priority Data

Mar. 28, 1980 [DE] Fed. Rep. of Germany ....... 3012012

[51] Int. Cl.³ .................... A61K 31/16; C07C 103/27; C07C 87/28
[52] U.S. Cl. .................................. 424/321; 424/330; 564/339; 564/221; 564/396; 568/329; 568/312; 568/314; 549/556
[58] Field of Search ................ 564/339, 221; 424/324, 424/330

[56] References Cited

U.S. PATENT DOCUMENTS

| 3,551,493 | 12/1970 | Ruschig et al. | 564/338 |
| 3,674,807 | 7/1972 | Buzzolini | 564/339 |
| 3,935,267 | 1/1976 | Hauck et al. | 564/338 |

FOREIGN PATENT DOCUMENTS

| 877481 | 7/1979 | Belgium | 564/339 |
| 2210842 | 9/1972 | Fed. Rep. of Germany | 564/339 |
| 2636725 | 2/1978 | Fed. Rep. of Germany | 564/339 |
| 2811638 | 9/1979 | Fed. Rep. of Germany | 564/339 |
| 1215751 | 12/1970 | United Kingdom | 564/339 |

*Primary Examiner*—James H. Reamer
*Attorney, Agent, or Firm*—Jordan B. Bierman; Linda G. Bierman

[57] ABSTRACT

There is disclosed substituted alkenones of Formula I

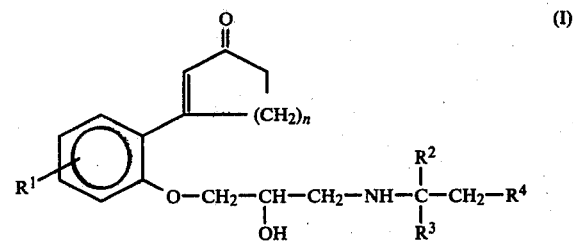

wherein
$R^1$ is alkyl or acylamino each having 1 to 4 carbon atoms, hydrogen, or halogen,
$R^2$ and $R^3$ individually are hydrogen, methyl or ethyl,
$R^4$ is hydrogen or dimethoxyphenyl, and
n is 1 or 2, or physiologically acceptable acid addition salts thereof. Intermediates are also disclosed, along with methods of preparation of both the intermediates and the end products.

The end products are useful as β adrenolytic and antihypertensive agents. They are useful in the treatment of angina pectoris, hypertension, and arrhythmia.

12 Claims, No Drawings

SUBSTITUTED 3-ARYL-2-CYCLOALKEN-1-ONE AND METHOD OF PREPARATION THEREOF

This application claims the priority of German P 30 12 012.8, filed Mar. 28, 1980.

The present invention is directed to novel alkenones and intermediates therefor which possess desirable therapeutic properties. In addition, the invention encompasses methods of preparation of both the intermediates and the end products.

The pharmaceutically active compounds of the present invention comprise alkenones of the Formula I

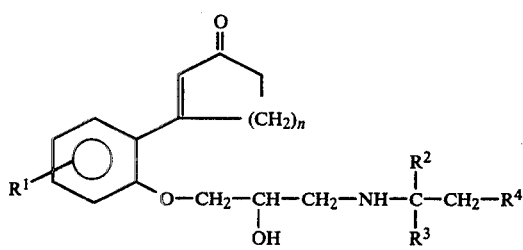

wherein $R^1$ is alkyl or acylamino each having 1 to 4 carbon atoms, hydrogen, or halogen. $R^2$ and $R^3$ are individually hydrogen, methyl, or ethyl, $R^4$ is hydrogen or dimethoxyphenyl, and n is 1 or 2. The invention also includes the physiologically or pharmaceutically acceptable acid addition salts of these compounds.

The novel substances are characterized by β adrenolytic and antihypertensive action; they are useful in the treatment of angina pectoris, hypertension, and arrhythmia. The dosage in man is 5 mg to 200 mg per day, per person. The preferred dose is 5 mg to 50 mg per day, per person.

As is well recognized in the art, the daily dose must be determined on an individual basis, since it depends upon the receptive sensitivity and the reactions of the patient. The treatment is preferably started with low doses, which are gradually increased, while the patient is being monitored by the physician.

For hypertension, the preferred doses are 10 mg to 20 mg given daily. Angina is preferably treated at a level of 5 mg to 10 mg. Arrhythmia is treated with 20 mg to 40 mg per day, per person. In the case of hypertension and angina, it is preferred to give the medicine in a single dose each day, while arrhythmia is best treated by dividing the dose in half and administering it twice a day.

It has been found that the effectiveness of the compounds of the present invention depends to some extent upon the position of the $R^1$ substituent with relation to the propoxy side chain. Those compounds wherein $R^1$ is meta to the side chain have been found to be particularly valuable. In addition, the compounds which have a t-butylamino group as the 3-alkylamino group of the side chain are also especially useful.

The compounds can be used as such, or in the form of their acid addition salts, if desired. They can be mixed with suitable solid or liquid pharmaceutically acceptable vehicles or diluents and administered by injections or orally. In the latter case, they are preferably in the form of dragees, tablets, or liquids. Among the suitable vehicles are lactose, gelatin, corn starch, stearic acid, ethanol, propylene glycol, ethers of tetrahydrofuryl alcohol, and water.

Also novel are the compounds of Formula II

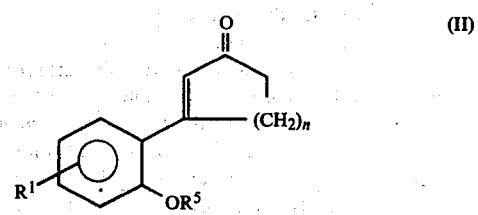

wherein $R^5$ is hydrogen, benzyl,

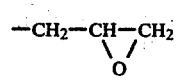

or

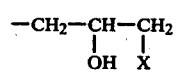

wherein X is chlorine or bromine. These compounds are useful as intermediates for the preparation of the compounds of Formula I heretofore described.

The compounds of Formula I are prepared by the reaction of the compounds of Formulas III and IV

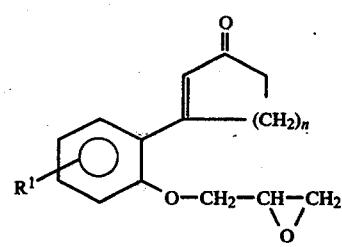

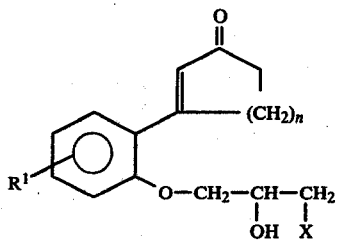

with an amine of Formula V.

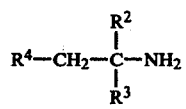

The reaction is carried out in an alcohol, preferably t-butanol, with excess amine at temperatures of 20° to 60° C. If desired, the free bases can be converted in the usual manner into their corresponding acid addition salts. Such acids as hydrochloric, hydrobromic, sulfuric, oxalic, fumaric, or maleic have been found suitable.

Compounds of formulas III and IV can be prepared from those compounds of Formula II wherein $R^5$ is hydrogen. These phenols can be obtained from the corresponding benzyl ethers and can be reacted with epichlorohydrin or epibromohydrin to form a mixture of the compounds of Formulas III and IV. It is possible to separate these mixtures by column chromatography, but this is not usually necessary.

The reaction is carried out using an excess of epihalogenohydrin in the presence of a catalytic amount of an organic base, or in the presence of an acid-binding agent; e.g. sodium hydroxide or potassium carbonate, in suitable solvents such as alcohols. It has been found that the reactions are accelerated by heating to 50° to 100° C. The benzyl ethers according to Formula II ($R^5$ is benzyl) are preferably split by treatment with hydrogen bromide/glacial acetic acid mixtures at room temperature.

The compounds of Formula II, wherein $R^5$ is benzyl, can be prepared by Grignard reaction of a phenol ether of Formula VI

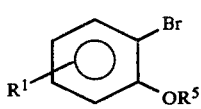

wherein $R^1$ is as set forth above, with an alkenone of Formula VII

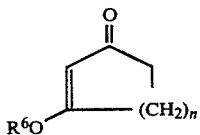

wherein $R^6$ denotes a methyl or ethyl group and n is 1 or 2. This reaction can be carried out in an ether, preferably tetrahydrofuran, as the solvent at boiling temperature. The compounds of Formula VI are either known or can be produced according to analogous methods. The compounds of Formula VII are also known from the literature.

As an alternative method for the preparation of the compounds of Formula II, a dione of Formula VIII

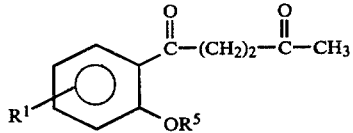

wherein $R^1$ is as set forth above, and $R^5$ is benzyl, is subjected to alkaline cyclization. This method produces cyclopentenones according to the present invention.

In turn, the compounds of Formula VIII are obtained from 2-halogen-acetophenones of Formula IX

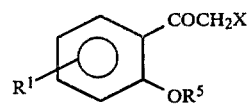

wherein $R^1$ is as set forth above, $R^5$ is benzyl, and X is chlorine or bromine. Such a compound is reacted with an alkali salt of acetoacetic methyl or ethyl ester to produce a dione of Formula X

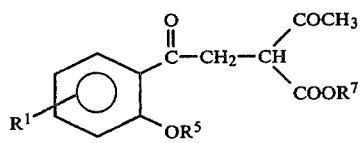

wherein $R^7$ is methyl or ethyl. Formula X is then saponified and decarboxylated with alkali to produce the diketones of Formula VIII. The compounds of Formula IX are known or obtainable according to known methods described in the literature.

The following Examples illustrate the invention.

EXAMPLE 1

3-[2-(2-hydroxy-3-tert.-butylamino-propoxy)-phenyl]-2-cyclopenten-1-one 2.0 g 3-(2-hydroxyphenyl)-2-cyclopenten-1-one are stirred with 30 ml epibromohydrin and catalytic amounts of piperidine for 1 hour at 100° C. After concentration, the mixture of epoxy- and bromohydrin is separated by high-pressure liquid chromatography. In this manner, 2 g 3-[2-(2,3-epoxypropoxy)-phenyl]-2-cyclopenten-1-one are obtained as an oil which is then dissolved in 20 ml t-butanol. 2 ml of t-butylamine were added and the mixture is stirred at room temperature for 48 hours.

After the solvent has evaporated, the residue is taken up in 2 N HCl and extracted with methylene chloride. The aqueous phase is made alkaline with 2 N NaOH and extracted with methylene chloride. The extracts are dried, mixed with ethanolic HCl, and evaporated down. The oil residue is dissolved in hot ethanol and mixed with acetic ester until it becomes cloudy. The hydrochloride of the 3-[2-(2-hydroxy-3-tert.-butylamino-propoxy)-phenyl]-2-cyclopenten-1-one crystallizes slowly. Melting point: 183–184 deg.C.

The compounds listed in Table 1 are prepared in an analogous manner.

TABLE 1

| Example No. | $R^1$ | $R^2$ | $R^3$ | $R^4$ | n | M.p. °C. | Salt |
|---|---|---|---|---|---|---|---|
| 2 | H | CH$_3$ | H | H | 1 | 185–187 | Hydrochloride |
| 3 | H | CH$_3$ | CH$_3$ | H | 2 | 186–187 | Hydrochloride |
| 4 | 4-CH$_3$ | CH$_3$ | CH$_3$ | H | 1 | 198–203 | Hydrochloride |
| 5 | 4-Cl | CH$_3$ | CH$_3$ | H | 1 | 218–222 | Hydrochloride |
| 6 | 4-F | CH$_3$ | CH$_3$ | H | 1 | 222–226 | Hydrochloride |
| 7 | 5-CH$_3$CONH- | CH$_3$ | CH$_3$ | H | 1 | 218–220 | Fumarate |

TABLE 1-continued

| Example No. | R¹ | R² | R³ | R⁴ | n | M.p. °C. | Salt |
|---|---|---|---|---|---|---|---|
| 8 | H | H | H | CH₃O— 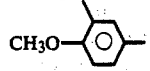 —; CH₃O— | 1 | 191–192 (decomp.) | Hydrochloride |

EXAMPLE 9

3-(2-hydroxyphenyl)-2-cyclopenten-1-one (a) 43.0 g (0.33 mole) acetoacetic ethyl ester are added dropwise under nitrogen to a suspension of 7.9 g sodium hydride in 250 ml absolute toluene at 50°–60° C. After the evolution of hydrogen is completed, 91.5 g (0.3 mole) 2-benzyloxyphenacylbromide in 400 ml toluene are added dropwise at 40° to 60° C. and subsequently heated to a boil for 2 hours. After filtration of the sodium bromide, the toluene solution is washed repeatedly with water, dried over MgSO₄, and evaporated down.

100 g of an oil which was identified by NMR-spectroscopy as 1-(2-benzyloxy-phenyl)-3-carbethoxy-pentane-1,4-dione is obtained.

(b) 85 g of compound (a) are heated to 100° C. with 3000 ml of 2% NaOH for 2.5 hours under nitrogen. After filtration of the precipitate which forms, the product is extracted with methylene chloride, and the organic phase is washed with water and dried over MgSO₄. Distillation of the methylene chloride residue (b.p.-$_{0.2}$ 210°–215° C.) yields a mixture of 65% 1-(2-benzyloxy-phenyl)-pentane-1,4-dione and 35% 3-(benzyloxy-phenyl)-2-cyclopenten-1-one.

36 g of the mixture of diketone and cyclopentenone are heated to a boil with 1.5 l of 5% NaOH for 18 hours under nitrogen. After extraction with methylene chloride and the usual treatment and recrystallization from acetic ester/ether, 21.4 g 3-(2-benzyloxy-phenyl)-2-cyclopenten-1-one are obtained having a melting point of 83°–84° C.

(c) 8.0 g 3-(2-benzyloxy-phenyl)-2-cyclopenten-1-one are stirred in 80 ml of 20% HBr/glacial acetic acid for 1 hour at room temperature. After evaporation of the glacial acetic acid, the residue is dissolved in methylene chloride and neutralized by shaking with a sodium-hydrogen-carbonate solution. After recrystallization from diisopropyl ether/diethyl ether, 3.7 g of 3-(2-hydroxyphenol)-2-cyclopenten-1-one are obtained with a melting point of 162°–165° C.

The compounds listed in Table 2 are prepared in a manner analogous to that of Example 9. In all cases set forth in the Table, n is 1.

TABLE 2

| Example No. | R¹ | R⁵ | M.p. °C. |
|---|---|---|---|
| 10 | 4-CH₃ | —CH₂C₆H₅ | 131–132 |
| 11 | 4-CH₃ | H | 187–189 |
| 12 | 4-Cl | —CH₂C₆H₅ | 94–95 |
| 13 | 4-Cl | H | 170–171 |
| 14 | 4-F | —CH₂C₆H₅ | 104–105 |
| 15 | 4-F | H | 157–159 |
| 16 | 5-NHCOCH₃ | —CH₂C₆H₅ | 165–167 |
| 17 | 5-NHCOCH₃ | H | 254–258 |

EXAMPLE 18

3-(2-hydroxyphenyl)-2-cyclohexen-1-one (a) 32.9 g (0.125 mole) of 2-benzyloxy-bromobenzene are added slowly dropwise, under stirring to 3.3 g (0.135 mole) of magnesium chips in 80 ml absolute tetrahydrofuran, and the resultant mixture is heated for 5 hours to a boil. The solution is then cooled to 20° C. and, within 30 minutes, 18.2 g (0.13 mole) of 3-ethoxy-2-cyclohexen-1-one are added dropwise at 20° to 25° C. After heating for 1 hour at boiling, the product is poured over about 500 ml saturated ammonium chloride solution and extracted with chloroform. After recrystallization from diisopropyl ether, 19.2 g 3-(2-benzyloxy-phenyl)-2-cyclohexen-1-one are obtained.

(b) 11.0 g 3-(2-benzyloxy-phenyl)-2-cyclohexen-1-one were stirred in 120 ml of 20% HBr/glacial acetic acid for 1 hour at room temperature. After evaporation of the glacial acetic acid, the residue is dissolved in methylene chloride, neutralized with NaHCO₃ solution and the CH₂Cl₂ residue is recrystallized from diisopropyl ether.

Yield: 5.3 g 3-(2-hydroxyphenyl)-2-cyclohexen-1-one with a melting point of 126° to 128° C.

EXAMPLE 19

Manufacture of tablets

Tablets which contain the ingredients indicated below are produced according to known procedures. These are for the treatment of hypertension at a dose level of 15 mg once a day, for the treatment of angina pectoris at 10 mg once a day, and for the treatment of arrhythmia at 15 mg twice daily.

|  | Tablet A | Tablet B |
|---|---|---|
| 3-[2-(2-hydroxy-3-tert.butyl-aminopropoxy)-4-chlorophenyl]-2-cyclopenten-1-one-hydrochloride (Example 5) | 5 mg | 10 mg |
| lactose | 89 mg | 84 mg |
| corn starch | 5 mg | 5 mg |
| magnesium stearate | 1 mg | 1 mg |

EXAMPLE 20

Manufacture of tablets

Tablets which contains the ingredients listed below are produced according to known procedures. These are for the treatment of hypertonia at a dosage level of 15 mg once a day, for the treatment of angina pectoris at 10 mg once a day, and for the treatment of arrhythmia at 15 mg twice daily.

|  | Tablet A | Tablet B |
|---|---|---|
| 3-[2-(2-hydroxy-3-tert.butyl-aminopropoxy)-4-fluorphenyl-2-cyclopenten-1-one hydrochloride (Example 6) | 5 mg | 10 mg |

| | Tablet A | Tablet B |
| --- | --- | --- |
| lactose | 89 mg | 84 mg |
| corn starch | 5 mg | 5 mg |
| magnesium stearate | 1 mg | 1 mg |

While only a limited number of specific embodiments of this invention have been expressly disclosed, it is, nonetheless, to be broadly construed, and not to be limited except by the character of the claims appended hereto.

What I claim is:

1. A substituted alkenone of Formula I

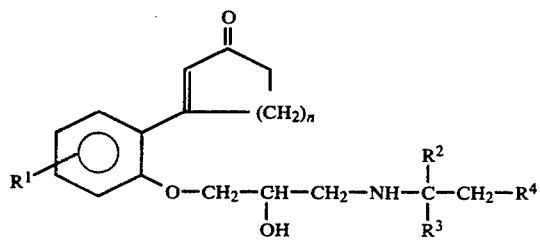

wherein $R^1$ is alkyl or acylamino each having 1 to 4 carbon atoms, hydrogen, or halogen, $R^2$ and $R^3$ individually are hydrogen, methyl or ethyl, $R^4$ is hydrogen or dimethoxyphenyl, and n is 1 or 2 or physiologically acceptable acid addition salts thereof.

2. The alkenone of claim 1 wherein $R^1$ is meta to the side chain.

3. The alkenone of claim 1 wherein $R^1$ is hydrogen, $R^2$ and $R^3$ are $CH_3$, $R^4$ is hydrogen, and n is 1.

4. The alkenone of claim 1 wherein $R^1$ is hydrogen, $R^2$ is $CH_3$, $R^3$ is hydrogen, $R^4$ is hydrogen, and n is 1.

5. The alkenone of claim 1 wherein $R^1$ is hydrogen, $R^2$ and $R^3$ are $CH_3$, $R^4$ is hydrogen, and n is 2.

6. The alkenone of claim 1 wherein $R^1$ is 4—$CH_3$, $R^2$ and $R^3$ are $CH_3$, $R^4$ is hydrogen, and n is 1.

7. The alkenone of claim 1 wherein $R^1$ is 4—Cl, $R^2$ and $R^3$ are $CH_3$, $R^4$ is hydrogen, and n is 1.

8. The alkenone of claim 1 wherein $R^1$ is 4—F, $R^2$ and $R^3$ are $CH_3$, $R^4$ is hydrogen, and n is 1.

9. The alkenone of claim 1 wherein $R^1$ is 5—$CH_3CONH$—, $R^2$ and $R^3$ are $CH_3$, $R^4$ is hydrogen, and n is 1.

10. The alkenone of claim 1 wherein $R^1$, $R^2$, and $R^3$ are hydrogen, $R^4$ is 3,4 dimethoxyphenyl, and n is 1.

11. A pharmaceutical composition for the treatment of angina pectoris, hypertension, or arrhythmia comprising an amount of the alkanone of claim 1 such that, when administered to a warm blooded animal, an effective dose will be provided in said animal, and a pharmaceutically acceptable carrier.

12. The method of treating angina pectoris, hypertension or arrhythmia comprising administering, to a warm blooded animal, an effective amount of the alkenone of claim 1.

* * * * *